(12) United States Patent
Hakamata (10) Patent No.: US 7,083,280 B2
(45) Date of Patent: Aug. 1, 2006

(54) PUPIL MEASURING APPARATUS

(75) Inventor: Naotoshi Hakamata, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 138 days.

(21) Appl. No.: 10/336,782

(22) Filed: Jan. 6, 2003

(65) Prior Publication Data

US 2003/0098951 A1    May 29, 2003

Related U.S. Application Data

(63) Continuation-in-part of application No. PCT/JP01/05880, filed on Jul. 6, 2001.

(30) Foreign Application Priority Data

Jul. 7, 2000    (JP) .......................... P2000-207216

(51) Int. Cl.
*A61B 3/14* (2006.01)
*A61B 3/10* (2006.01)
*A61B 3/00* (2006.01)

(52) U.S. Cl. ...................... 351/209; 351/200; 351/204; 351/205; 351/221; 351/246

(58) Field of Classification Search .............. 351/200, 351/204–211, 213–216, 221, 246; 600/558
See application file for complete search history.

(56) References Cited

U.S. PATENT DOCUMENTS

| | | | |
|---|---|---|---|
| 4,850,691 A | 7/1989 | Gardner et al. .............. 351/221 |
| 5,196,873 A | 3/1993 | Yamanobe et al. ......... 351/210 |
| 5,410,376 A * | 4/1995 | Cornsweet et al. ......... 351/210 |
| 5,422,690 A | 6/1995 | Rothberg et al. ........... 351/209 |
| 5,661,538 A * | 8/1997 | Carter ........................ 351/237 |
| 5,777,718 A * | 7/1998 | Kohayakawa ................ 351/211 |
| 5,883,691 A | 3/1999 | Ishikawa et al. ............. 351/222 |
| 6,089,714 A * | 7/2000 | Galiana et al. ............. 351/202 |
| 6,206,522 B1 * | 3/2001 | Maloney et al. ............. 351/205 |
| 6,217,172 B1 | 4/2001 | Shibutani et al. ........... 351/204 |

FOREIGN PATENT DOCUMENTS

| | | |
|---|---|---|
| EP | 0 456 166 A1 | 11/1991 |
| EP | 0 743 041 A1 | 11/1996 |
| JP | HEI04-015032 | 3/1993 |
| JP | HEI09-28672 | 2/1997 |
| JP | 11-225966 | 8/1999 |
| JP | HEI11-225966 | 8/1999 |
| JP | 2000-262475 | 9/2000 |

* cited by examiner

*Primary Examiner*—Ali Iman
*Assistant Examiner*—John R. Sanders
(74) *Attorney, Agent, or Firm*—Drinker, Biddle & Reath LLP

(57) ABSTRACT

A pupil measuring apparatus includes a mark placed in a space where a background is observable by both eyes; a mark moving device for moving the mark between the eyes and the background; an illumination optical system for illuminating the eyes from the background side; two cameras for respectively imaging the pupils of the eyes; a calculating means for calculating areas or diameters of the respective pupils thus imaged, from video signals of the two cameras; and a display for providing an output of a graph showing change in the areas or diameters of the two pupils calculated against a position of the mark or a time associated with the position on a single screen.

11 Claims, 6 Drawing Sheets

PUPIL MEASURING APPARATUS

RELATED APPLICATION

This is a continuation-in-part application of application Serial no. PCT/JP01/05880 filed on Jul. 6, 2001, now pending

TECHNICAL FIELD

The present invention relates to pupil measuring apparatus (pupillometer).

BACKGROUND ART

The medical treatment for such disease as cataract and the like is to replace an opaque crystalline lens with an artificial lens. In order to determine the vision before and after the replacement, there are demands for apparatus for measuring the pupillary accommodation ability (near reflex), and such apparatus is configured to measure the pupillary areas of the respective eyes on a single-eye basis. In the measurement, a subject is made to view a mark and the papillary area in that state is measured.

DISCLOSURE OF THE INVENTION

However, the near reflex means significant with the left and right eyes open, and the foregoing conventional apparatus did not allow measurement of effective near reflex. The near reflex can also occur against the mark placed in a backgroundless state, but state change due to the near reflex appears more prominent when the mark to be viewed is placed at a position where the background is seen. The present invention has been accomplished in view of the above knowledge and an object of the invention is to provide pupil measuring apparatus that permits effective inspection of the near reflex.

In order to solve the above problem, a pupil measuring apparatus of the present invention comprises a mark moving device for moving a mark in a predetermined region from a reference position, the reference position being set at a position where two pupils are to be placed; an illumination optical system for illuminating the reference position; two cameras for respectively imaging the two pupils placed at the reference position; calculating means for calculating pupillary areas, pupillary diameters, or pupillary positions of the respective pupils thus imaged, from video signals of the two cameras; and a display for presenting an output of a graph of change in the pupillary areas, pupillary diameters, or pupillary positions thus calculated, against a position of the mark or a time associated with the position, on a single screen.

The present invention is characterized in that the calculating means performs a predetermined operation on the calculated pupillary areas, pupillary diameters, or pupillary positions and/or the mark position or time yielding these and displays the result of the operation on the display. In this case, it is feasible to quickly and quantitatively keep track of the result of the operation. Particularly, when a background is observable farther over the mark from the reference position, the state change due to the near reflex becomes more prominent. The pupils (eyes) placed at the reference position are preferably illuminated from the background side by an illumination optical system.

The present invention is characterized in that the calculating means displays the video signals together with the graph in a superimposed state on the displays In this case, it is feasible to check states of the two pupils while quickly and quantitatively keeping track of the values obtained by the foregoing operation.

Another pupil measuring apparatus of the present invention is a pupillometer comprising a mark placed in a space in which a background is observable from a reference position, the reference position being set at a position where two pupils are to be placed; a mark moving device for moving the mark in a predetermined region between the reference position and the background; an illumination optical system for illuminating the reference position from the background side; and two cameras for respectively imaging the two pupils placed at the reference position, wherein the illumination optical system comprises at least three light emitting diodes for illuminating each of the pupils from at least three directions. Two properly selected out of these three light emitting diodes are preferably spaced from each other along a horizontal direction. Light emitted from the light emitting diodes is preferably infrared light, in order to exercise no effect on constriction of the pupils.

BEST MODE FOR CARRYING OUT THE INVENTION

The pupil measuring apparatus as embodiments will be described below. The same elements will be denoted by the same reference symbols and redundant description will be omitted.

Figure 1:
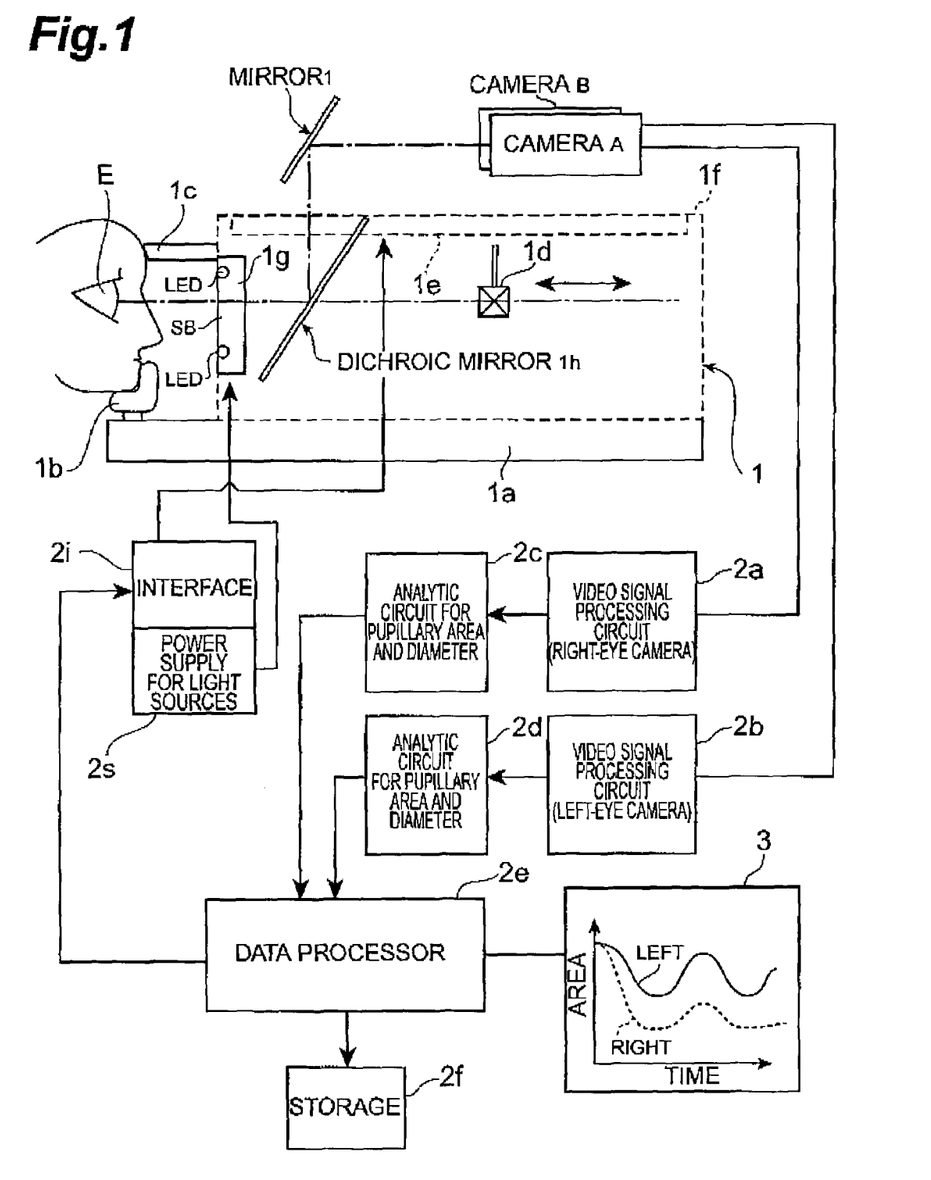
FIG. 1 is a block diagram of a pupillometer as an embodiment.

FIG. 1 is a block diagram of a pupillometer as an embodiment. The jaw of subject's head is mounted on a jaw seat 1b fixed on a surface of base 1a of target presenting portion 1. In this case, the subject's forehead goes into contact with a forehead receiver 1c mounted on the front side of the target presenting portion 1. A reference position is set at the position of the subject's eyes E in this state.

The position of the forehead receiver 1c is adjustable along the longitudinal direction (which will be defined as a direction X) of the target presenting portion 1. The target presenting portion 1 is provided with a mark 1d moving along the direction X. The mark 1d is moved in the direction X by a mark moving device 1e.

Here the mark 1d is located inside an envelope 1f made of a semitransparent resin. The envelope is open at the two ends in the direction X, so that the background of the apparatus can be observed from the reference position.

An illumination optical system 1g is fixed on the front side of the envelope 1f, i.e., near the reference position where the two eyes E are placed. The illumination optical system 1g is constructed in structure in which a plurality of light emitting diodes LEDs to emit infrared light are mounted on a support board SB. The optical path is secured between the reference position and the mark 1d, so that the two subject's eyes E both can visually recognize the mark 1d together with the background. It is also possible to employ a configuration in which the light emitting diodes LEDs are mounted on a goggle, it is mounted on the subject's face, and dichroic mirrors are mounted in windows of the goggle.

When the light emitting diodes LEDs emit light, the two eyes E are simultaneously illuminated, and images of the respective eyes E are reflected by a dichroic mirror 1h placed in the envelope 1f, are then turned by a mirror 1i, and are simultaneously incident respectively into a CCD camera A and into a CCD camera B for imaging, respectively. Namely, the dichroic mirror 1h reflects the infrared light but transmits light from the mark 1d. When the mark 1d is illuminated with natural light or when the mark 1d itself emits visible light, the light from the mark 1d is visible light.

Video signals from the cameras A, B are fed into respective video signal processing circuits 2a, 2b for the right eye and for the left eye, which binarize the video signals. Specifically, since the pupils of the two eyes E are black, i.e., lower in reflectance than the surrounding areas, the binarizing operation results in extracting the two pupillary regions. The data of these pupillary regions obtained by the binarizing operation is fed into respective analytic circuits 2c, 2d, which perform analysis on pupillary areas, papillary diameters, and/or pupillary positions.

The analytic circuits 2c, 2d also receive the video signals themselves. The analytic circuits 2c, 2d calculate the pupillary areas, pupillary diameters, and/or pupillary positions and feed the result of the calculation to a data processing section 2e. The data processing section 2e also receives the video signals themselves.

The data processing section 2e receives a position signal indicating a position of the mark 1d and a time yielding the position, based on a signal from the mark moving device 1e. Therefore, the data processing section 2e receives the data of the pupillary areas, papillary diameters, and/or pupillary positions of the two eyes E, the data of the position and time of the mark 1d yielding the data, and the video signals of the two eyes E.

The data processing section 2e prepares a graph of the data of the pupillary areas, pupillary diameters, and/or pupillary positions of the two eyes E in association with the data of the position or time of the mark 1d, and displays the graph together with the video signals of the two eyes E (the images of the two eyes E) on a display 3. The display 3 in the same figure is illustrated as an example in which it displays only a graph showing the relation between pupillary areas and time.

The data processing section 2e is a computer, which controls through an interface 2i, supply of power from a power supply 2i to the light emitting diodes LEDs of the illumination optical system 1g and movement of the mark moving device 1e and which receives the position (information) of the mark 1d from the mark moving device 1e through the interface 2i. The data processing section 2e also measures the time necessitated for the movement, in conjunction with the position information. The position information and time can be a control amount and a control time of the mark moving device 1e. This position may change linearly against passing time, or may change logarithmically.

Figure 2:
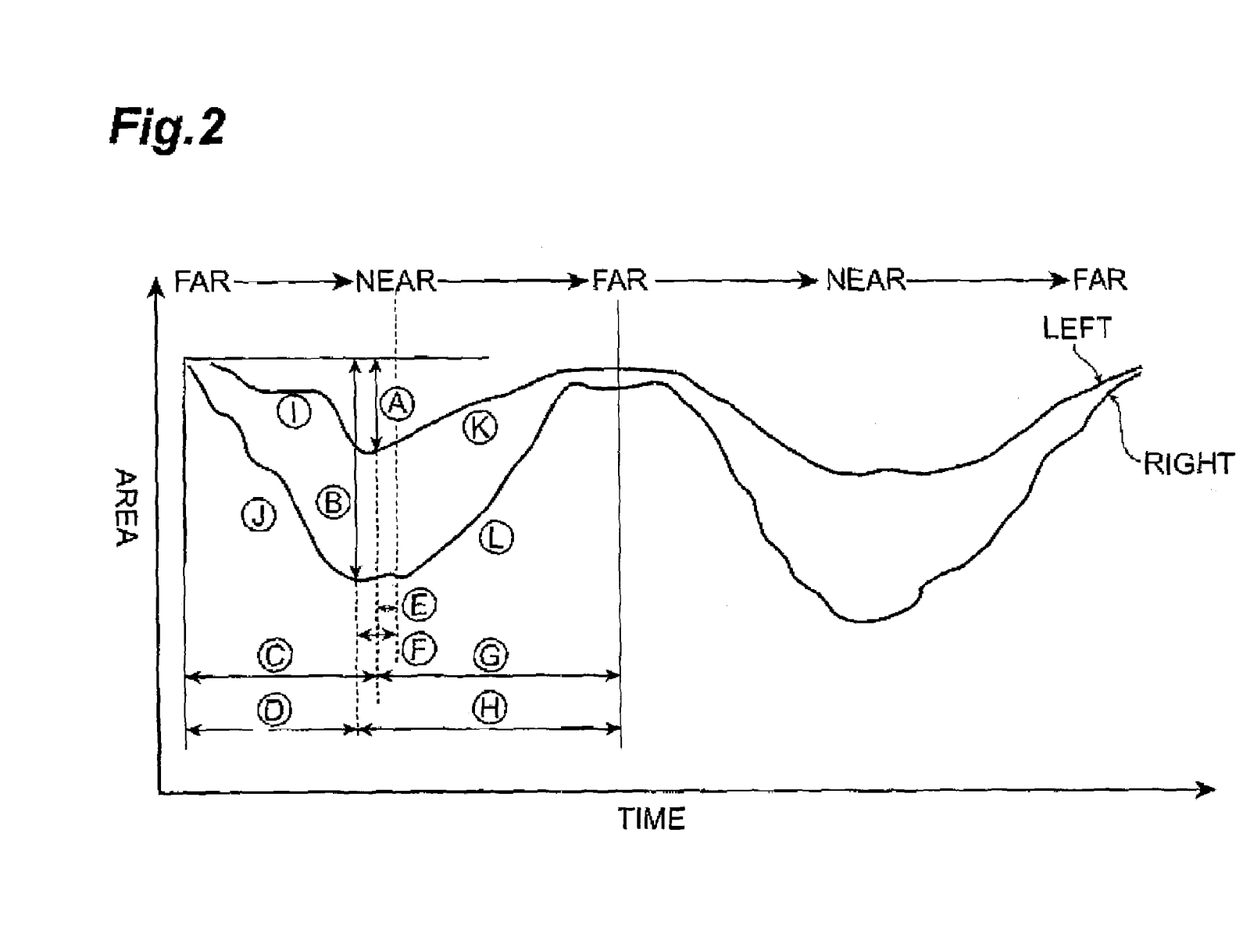
FIG. 2 is a graph displayed on display 3.

FIG. 2 is a graph displayed on the display 3. This graph shows the relation between passing time required for measurement and pupillary area. NEAR indicates a state in which the mark 1d is located near the subject, and FAR a state in which it is far. An initial state is defined as a state of the two eyes E with the mark FAR at a start of measurement. The mark 1d is moved by the mark moving device 1e, and in the present example, the mark 1d is moved from FAR to NEAR is and thereafter is moved again to FAR, NEAR, and FAR. Namely, the mark 1d undergoes back-and-forth motion along the direction X.

In the same figure, A indicates a left-eye miosis amount (initial pupillary area—minimum), and the left-eye miosis amount to the area of the pupil in the initial state represents a left miosis rate. B indicates a right-eye miosis amount (initial pupillary area—minimum) and a miosis rate is calculated therefrom. C indicates a left-eye miosis time (a time in the initial state—a time yielding the minimum), D a right-eye miosis time (a time in the initial state—a time yielding the minimum), E a time difference between a position of a near point subjectively recognized by the left eye (a time when the mark 1d is at the nearest point) and a maximum miosis point (the time yielding the minimum), F a time difference between a position of a near point subjectively recognized by the right eye and a maximum miosis point, G a left-eye mydriasis time (the time yielding the minimum—a time for subsequent movement of the mark 1d to FAR), H a right-eye mydriasis time, and I to K maximum reaction speeds (maximums of time differential of area or diameter).

The apparatus may also be configured so that the calculating means 2a to 2e obtains the difference at the same position or time between the two areas or diameters calculated and displays the obtained value on the display 3. By defining this function as a cursor function, it is feasible to check the pupils and the areas or diameters thereof at arbitrary timing (time) on the display 3.

The apparatus may also be configured so that the calculating means 2a to 2e obtains minimums of the two areas or diameters calculated with respect to the position or time, calculates the difference (F–E) between positions or times yielding these minimums, and displays the obtained value on the display 3. The above graph and parameters are stored in a storage device 2f.

The near reflex is reaction occurring while the two eyes E track the target (index: mark) 1d moving far and near, and the neural activity in the cerebral cortex is considered to exercise a significant effect on exhibition of the function of recognizing and tracking the mark 1d. It is known that the efferent path of near reflex passes the episclera intramembranous ganglia, and the analysis on the near reflex indicated by foregoing A to K allows us to grasp the status of the nerve system different from the light reflex inspection.

The parameters A, B indicating the strength of reaction and the parameters C, D, G, H indicating the times taken for the reaction are considered to reflect the status of the nerve system, and the reaction becomes stronger if the nerve path is in good order.

The target distance difference (or time difference) between the position of the near point subjectively recognized and the maximum point of pupillary reaction like the parameters E, F is considered to indicate the accommodation ability by the near reflex. Namely, it is considered that with high ability of recognizing the mark 1d moving in the depth direction (direction X), the near reflex occurs to a possible farthest point from the near point position subjectively recognized.

Since the present apparatus provides the display of the parameters about the two eyes E, it is feasible to quantitatively capture the state of near reflex and, as a result, it is also feasible to perform inspection including cranial nerve function testing.

Figure 3:
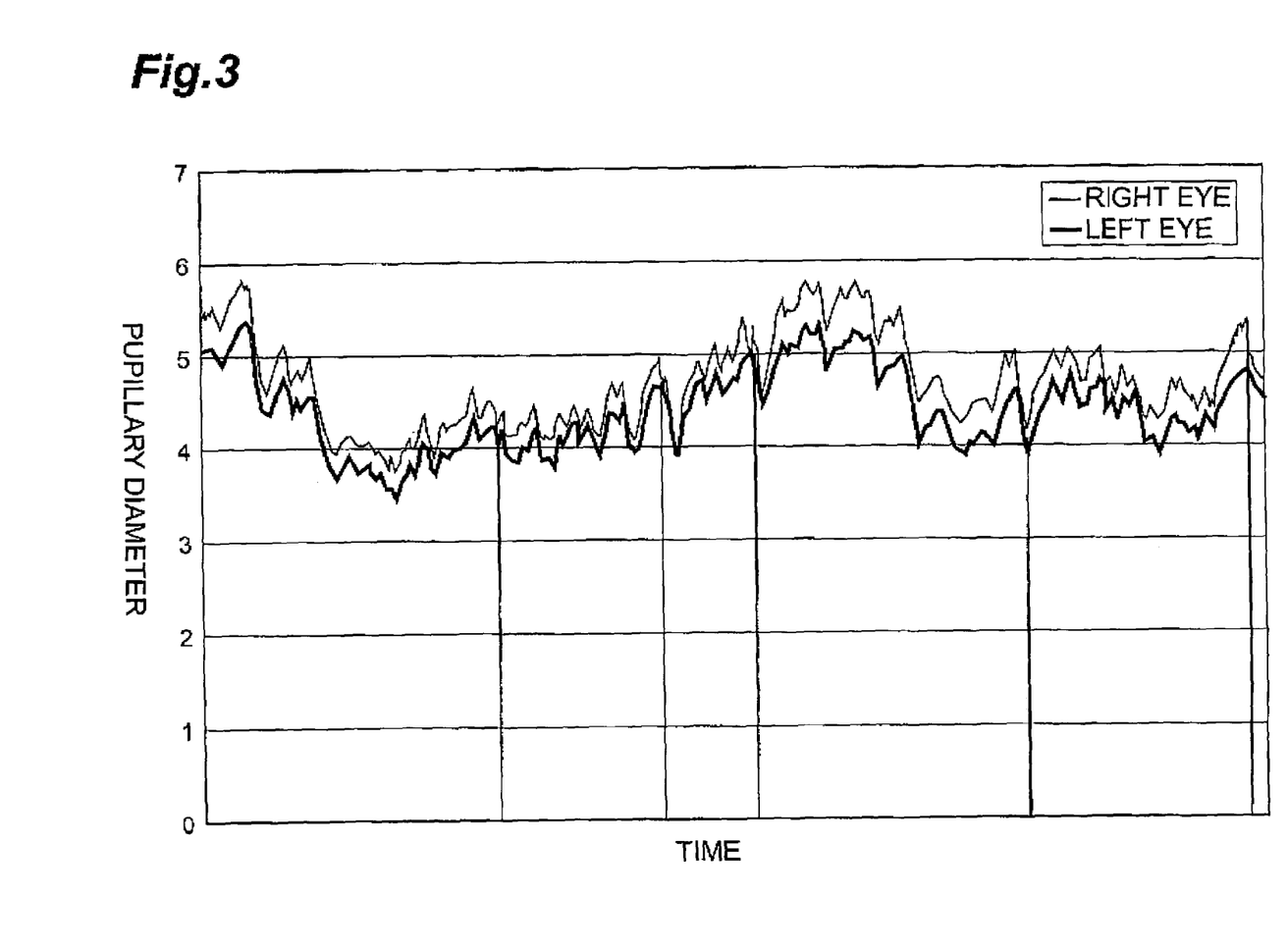
FIG. 3 is a graph showing the relation between measured time and diameters of pupils of the two eyes.

FIG. 3 is a graph showing the relation between measured time and diameters (mm) of the pupils of the two eyes in measurement for a subject by the foregoing apparatus. As apparent from the same graph, when the mark 1d is moved in a background-observable state, the diameters of the two eyes E exhibit prominent change and the near reflex is clearly measured.

As described above, the foregoing pupillometer comprises the mark 1d placed in the space where the background is observable from the reference position, the reference position being set at the position where the two pupils PP (the two eyes E: cf. FIG. 4) are to be placed; the mark moving device 1e for moving the mark 1d in the predetermined region between the reference position and the background (FAR to NEAR); the illumination optical system 1g for simultaneously illuminating the reference position, i.e., the two eyes E from the background side; the two cameras A, B for respectively and simultaneously imaging the two pupils placed at the reference position; the calculating means 2a to 2e for calculating the areas or diameters of the respective pupils thus imaged, from the video signals of the two cameras A, B; and the display 3 for providing the output of the graph of change in the calculated areas or diameters against the position of the mark 1d or the time associated with the position, on the single screen.

The near reflex means significant when the left and right eyes E are open. The present apparatus is configured so that the two eyes F can recognize the background together with the mark 1d so as to change their pupillary areas or diameters and so that the graph is displayed with the display of the video signals of the two eyes E in this state. Therefore, the apparatus is able to measure the near reflex effectively. Since the calculating means 2a to 2e displays the graph of the near reflex on the display 3, the analysis is easy thereon.

Since the calculating means 2a to 2e performs the predetermined arithmetic operation on the calculated areas or diameters, or the position or time yielding them and displays the operation result A to K on the display 3, it is feasible to quickly and quantitatively keep track of them.

In the case where the calculating means 2a to 2e displays the video signals together with the graph in a superimposed state on the display 3, it is feasible to check the states of the two eyes (pupils) E while quickly and quantitatively keeping track of the values obtained by the foregoing operation.

A technique of detecting horizontal positions of the pupils will be described below.

Figure 4:
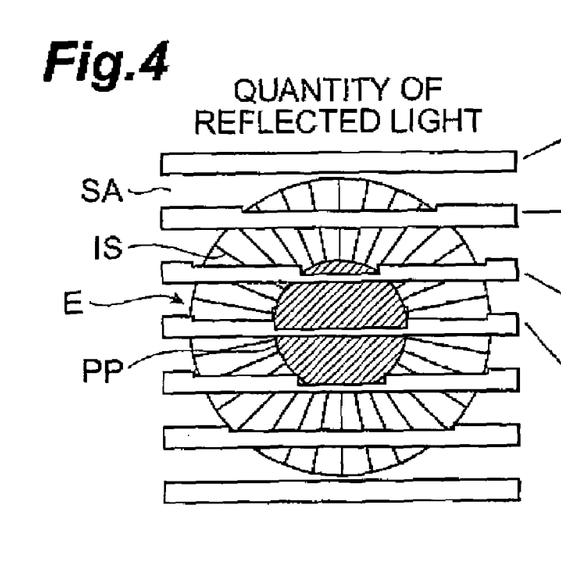
FIG. 4 is a diagram showing an image of an eye E imaged.

FIG. 4 is a diagram showing an image of an eye E imaged. There is an iris IS in a circular region except the sclera SA in the eye E and there is a round pupil PP in the center of the iris IS. The eye E is imaged by a solid-state image sensing device, and reflected light from the eye E is projected onto its image pickup surface. The image pickup surface is constructed of a plurality of vertical shift registers arranged in the horizontal direction, a string of charges stored at the same address (row) in the respective vertical shift registers constitutes a charge string of one horizontal line, and the image of the eye E projected onto the image pickup surface is sequentially read from every charge string of one horizontal line, so as to change the charge strings into a video signal. The higher the quantity of reflected light in the surface region of the eye E, the higher the level of the video signal; the lower the quantity of reflected light, the lower the level of the video signal. Namely, the level of the video signal indicates the luminance.

Figure 5A:
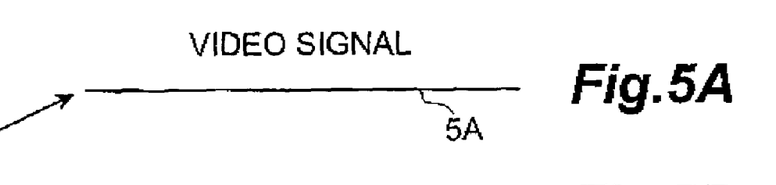
FIG. 5A, FIG. 5B, FIG. 5C, and FIG. 5D are timing charts showing the luminance of video signals.
Figure 5B:
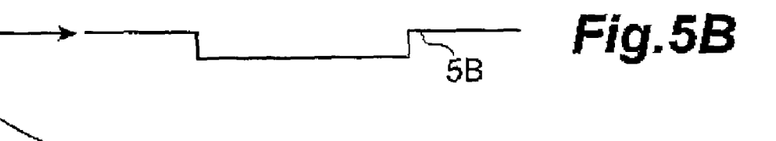
Figure 5C:
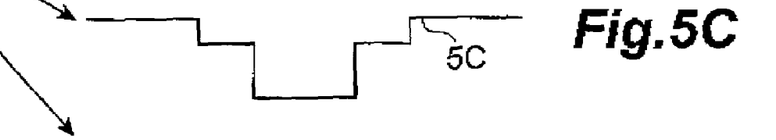
Figure 5D:
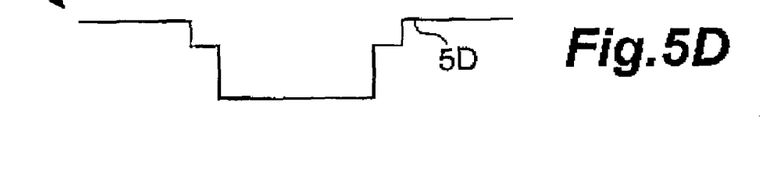

FIGS. 5A, 5B, 5C, and 5D are timing charts indicating the luminance of video signals. The quantity of reflected light on a horizontal line passing only the white sclera SA is always at a high level (FIG. 5A); on a horizontal line passing only the iris IS, the quantity of reflected light is at a middle level only on a line corresponding to the iris IS (FIG. 5B); on a horizontal line passing the sclera SA, iris IS, and pupil PP, the quantity of reflected light is at a high level, at a middle level, and at a low level, respectively (FIG. 5C or FIG. 5D). Levels of the video signals are determined in proportion to these reflected light quantity levels.

Figure 6:
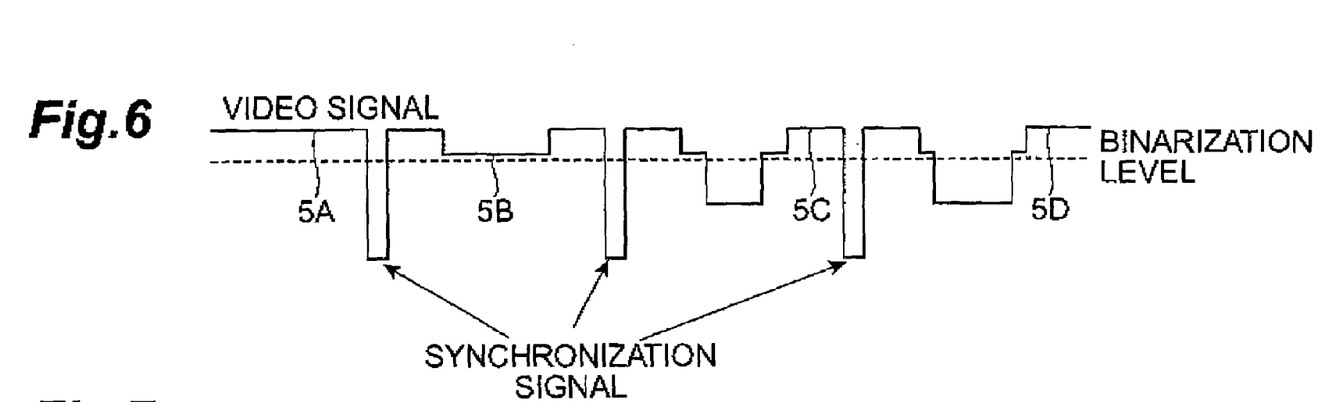
FIG. 6 is a timing chart showing the luminance of video signals outputted in time series.

FIG. 6 is a timing chart indicating the luminance of video signals outputted in time series. The video signals 5A, 5B, 5C, and 5D shown in FIGS. 5A, 5B, 5C, and 5D continuously appear in order, and synchronization signals of a black level are interposed between the video signals. A reference level is defined at a predetermined level that is lower than the luminance level of the video signal corresponding to the reflected light from the iris IS and that is higher than the luminance level of the video signal corresponding to the reflected light from the pupil PP. By performing a binarizing operation of the video signals on the basis of the reference level, only the luminance level corresponding to the pupil PP can be obtained as a low level.

Figure 7:
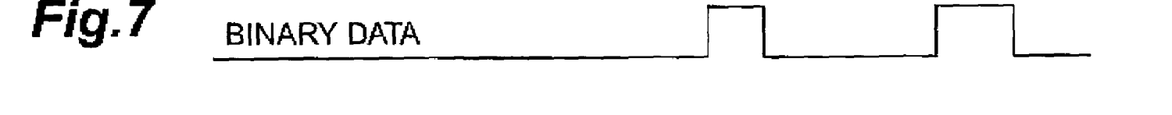
FIG. 7 is a timing chart of binary data outputted in time series.

FIG. 7 is a timing chart of binary data outputted in time series. In the present example, the binarizing operation is performed so as to reverse the levels, and thus the luminance level corresponding to the pupil PP is gained as a high level. The luminance level corresponding to the pupil PP constitutes one measured pulse per horizontal line, and the width of this measured pulse is proportional to the horizontal width of the pupil PP in the horizontal line corresponding thereto (the width at a specific vertical position).

This measured pulse is sequentially compared with a unit pulse having a reference pulse width and a number of unit pulses in the measured pulse with the logical product between them being a high level, is obtained as a width of the measured pulse. Widths of plural measured pulses are measured per frame.

An average is calculated for widths of measured pulses on four horizontal lines, and this average is stored. Then an average is calculated for widths of measured pulses on four continuous horizontal lines including a horizontal line located one line lower than the first four lines and this current average is compared with the stored average. When the current average is larger than the stored average, the current average is stored as a maximum. Thereafter, the like step is repeated in one frame arid the maximum is finally determined in one frame. The horizontal lines are read from top to bottom. The maximum can be treated as a horizontal pupillary diameter.

A center position of the width of the measured pulse on the lowermost horizontal line in the horizontal line set yielding the maximum, is stored as a horizontal position of the pupil PP. The number of horizontal lines constituting each horizontal line set does not always have to be four as long as it is plural.

Horizontal positions of the pupils PP are stored while the mark id shown in FIG. 1 is moved back and forth. A graph of these is displayed together with the position of the mark 1d on the display 3. Instead of the position of the mark 1d, it is also possible to use the time corresponding to the position. The horizontal pupillary diameters can be determined as described above, and the papillary areas are given each as the sum of pulse widths (which may be averages of pulse widths) existing in one frame.

As described above, the apparatus in the present example comprises the mark 1d placed in the space in which the background is observable from the reference position, the reference position being set at the position where the two pupils PP are to be placed; the mark moving device 1e for moving the mark 1d in the predetermined region between the reference position and the background; the illumination optical system 1g for illuminating the reference position from the background side; the two cameras A, B for respectively imaging the two pupils PP placed at the reference position; the calculating means for calculating the (pupillary areas, pupillary diameters, or) pupillary positions of the respective pupils PP thus imaged, from the video signals of the two cameras A, B; and the display 3 for providing the output of the graph of change in the calculated (pupillary areas, pupillary diameters, or) pupillary positions against the position of the mark 1d or the time associated with the position, on the single screen. The calculating means can be constructed of the processing circuits 2a, 2b and the analytic circuits 2c, 2d in FIG. 1.

Figure 8:
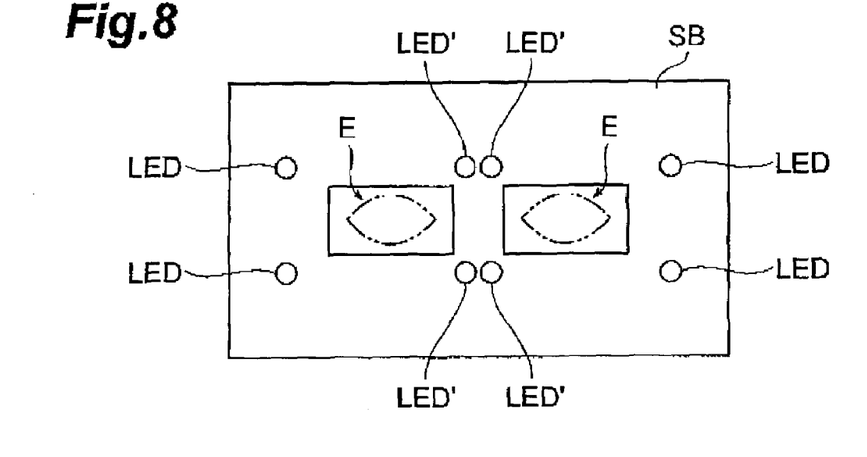
FIG. 8 is a front view of a support board to which main and auxiliary light emitting diodes are attached.

The illumination optical system 1g will be described below. As described previously, the illumination optical system 1g is provided with the support board SB.

FIG. 8 is a back view of the support board SB. In the peripheral area of the support board SB, four main light emitting diodes LEDs are mounted, and two imaging windows WINs are formed at positions corresponding to the respective eyes E. Four auxiliary light emitting diodes LED's are mounted in the region between the two imaging windows WINs (the region near the nose) in the support board SB.

Figure 9A:
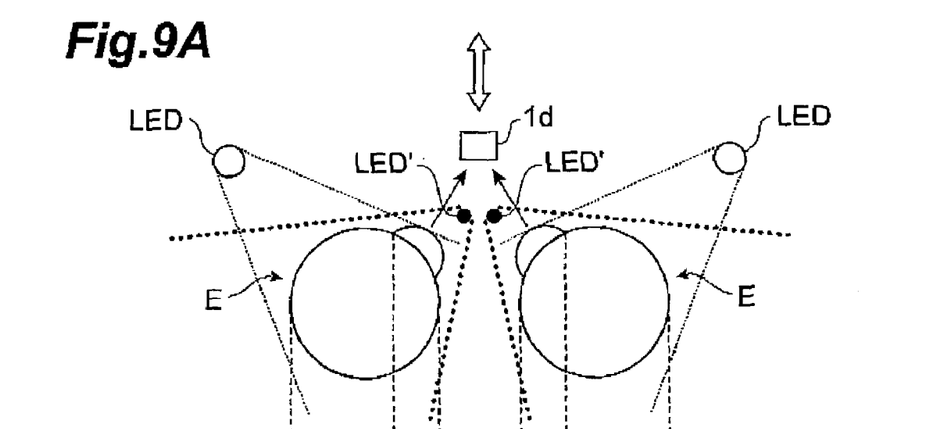
FIG. 9A is a diagram showing the relation between light emitting diodes and eyes.
Figure 9B:
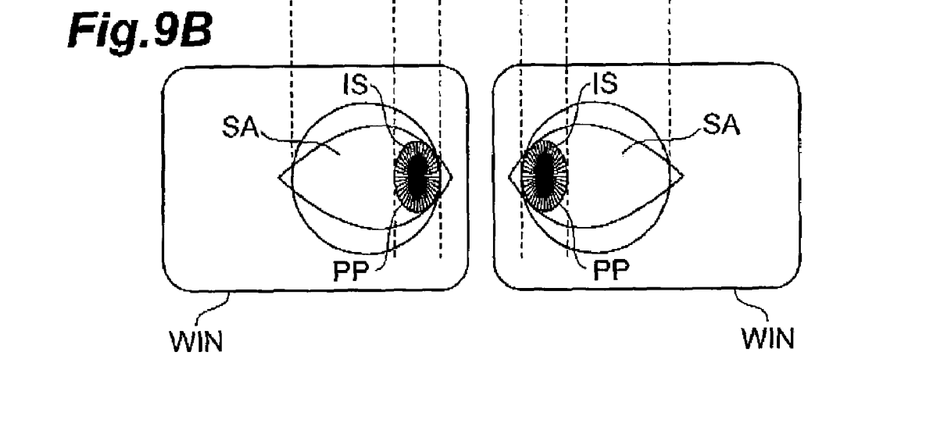
FIG. 9B is a diagram showing the eyes observed through imaging windows.

FIG. 9A is a diagram showing the relation between the light emitting diodes and the eyes, and FIG. 9B a diagram showing the eyes E observed through the imaging windows WINs. When the mark 1d is located near the both eyes E, the eyes E undergo convergence (i.e., the eyes rotate inward) and the pupils PP cannot be illuminated well with only the main light emitting diodes LEDs mounted in the peripheral area of the support board SB. Since in the present example the auxiliary light emitting diodes LED's located on the nose side are mounted on the support board SB, the pupils PP can be illuminated well even during periods of convergence reaction. It is noted that the auxiliary light emitting diodes LED's are located at positions off straight lines connecting the eyes E with the mark 1.

The auxiliary light emitting diodes LED's may be arranged one per eye E as long as they are located on the nose side. Namely, the illumination optical system 1g is provided with the light emitting diodes LEDs, LED's illuminating each of the pupils PP from at least three directions (four directions in the present example). In other words, the main light emitting diodes LEDs and the auxiliary light emitting diodes LED's are spaced from each other along the horizontal direction in illumination of each eye E. Namely, when three light emitting diodes per eye E are used for illumination, two properly selected out of these three light emitting diodes are spaced from each other along the horizontal direction.

Accordingly, the pupils PP can be uniformly illuminated even during periods of convergence reaction. The light emitted from the light emitting diodes is preferably infrared light, in order to exercise no effect on constriction of the pupils. As described above, the foregoing pupillometer permits effective inspection of the near reflex.

The reference level in the aforementioned binarizing operation can be varied in 0 to 255 steps, and it is also possible to alter the moving speed of the mark 1d, the number of forward and backward movements of the mark 1d, the near point distance of the mark 1d, and the moving range of the mark 1d. Therefore, the preferred measurement can be performed in conformity with each patient. When an ID number of a patient is fed into the data processing section before a start of the measurement, measured data can be placed in one-to-one correspondence to individual information.

INDUSTRIAL APPLICABILITY

The present invention is applicable to the pupil measuring apparatus.

What is claimed is:

1. A pupil measuring apparatus comprising:
a mark moving device for moving a position of a mark in a predetermined region from a reference position, said reference position being set at a position where two pupils are to be placed;
an illumination optical system for illuminating said reference position;
two cameras for respectively imaging said two pupils placed at said reference position;
calculating means for calculating pupillary areas, pupillary diameters, or pupillary positions of the respective pupils imaged, from video signals of the two cameras; and
a display for providing an output of a graph of change in said pupillary areas, pupillary diameters, or pupillary positions thus calculated against a position of said mark or a time associated with the position on a single screen; and
background, observable beyond said mark when viewed from said reference position, for changing said pupillary areas or said pupillary diameters as a result of the two pupils recognizing said background together with said mark, wherein a near reflex characteristic associated with said two pupils is measured more accurately as a result of said recognition by said pupils of said background, and said illumination optical system illuminates said reference position from said background side.

2. The pupil measuring apparatus according to claim 1, wherein said calculating means performs a predetermined operation on said pupillary areas, pupillary diameters, or pupillary positions thus calculated and/or the position or time of the mark yielding them, and displays the result of the operation on said display.

3. The pupil measuring apparatus according to claim 1, wherein said calculating means displays said video signals together with said graph in a superimposed state on said display.

4. The pupil measuring apparatus according to claim 1, comprising at least three light emitting diodes for respectively illuminating each of said pupils from at least three directions.

5. The pupil measuring apparatus according to claim 4, wherein two properly selected out of said three light emitting diodes are spaced from each other along a horizontal direction.

6. The pupil measuring methed apparatus according to claim 1,
wherein said mark moving device moves the mark position logarithmically.

7. The pupil measuring methed apparatus according to claim 1,
wherein said calculating means obtains the difference, at the same position of the mark or time corresponding to the mark position, between the two areas of the respective pupils or two diameters of the respective pupils and displays the obtained value on the display.

8. The pupil measuring methed apparatus according to claim 1,
wherein said calculating means obtains the minimums, at the same position of the mark or time corresponding to the mark position, of the two areas of the respective pupils or two diameters of the respective pupils and displays the obtained value on said display.

9. A pupil measuring method comprising the steps of:
moving a mark in a predetermined region from a reference position;
illuminating said reference position;
providing a background observable beyond said mark when viewed from said reference position;
using two cameras for respectively imaging two pupils located at said reference position, said background changing pupillary areas or pupillary diameters of said two pupils as a result of said two pupils recognizing said background together with said mark, wherein a near reflex characteristic associated with said two pupils is measured more accurately as a result of said recognition by said pupils of said background;
calculating said pupillary areas, said pupillary diameters, or pupillary positions of the respective pupils imaged, from video signals of the two cameras; and
displaying a graph of change in said pupillary areas, pupillary diameters, or pupillary positions thus calculated against a position of said mark or a time associated with the position on a single screen.

10. The pupil measuring method according to claim 9, further comprising the steps of displaying said video signals together with said graph in a superimposed state on a display.

11. The pupil measuring method according to claim 9, further comprising the steps of illuminating each of said pupils from at least three directions.

* * * * *